(12) United States Patent (10) Patent No.: US 9,040,098 B2
Schweizer et al. (45) Date of Patent: May 26, 2015

(54) SOLUBLE CANOLA PROTEIN ISOLATE PRODUCTION ("NUTRATEIN")

(71) Applicants: Martin Schweizer, Winnipeg (CA); Brent E. Green, Warren (CA); Kevin I. Segall, Winnipeg (CA); James Logie, Winnipeg (CA)

(72) Inventors: Martin Schweizer, Winnipeg (CA); Brent E. Green, Warren (CA); Kevin I. Segall, Winnipeg (CA); James Logie, Winnipeg (CA)

(73) Assignee: Burcon Nutrascience (MB) Corp., Winnipeg, Manitoba (CA)

( * ) Notice: Subject to any disclaimer, the term of this patent is extended or adjusted under 35 U.S.C. 154(b) by 0 days.

(21) Appl. No.: 13/922,313

(22) Filed: Jun. 20, 2013

(65) Prior Publication Data

US 2013/0281670 A1 Oct. 24, 2013

Related U.S. Application Data

(60) Division of application No. 12/588,318, filed on Oct. 13, 2009, now abandoned, which is a continuation-in-part of application No. 12/500,713, filed on Jul. 10, 2009, now Pat. No. 8,697,144.

(60) Provisional application No. 61/129,673, filed on Jul. 11, 2008.

(51) Int. Cl.
*A61K 36/185* (2006.01)
*A23L 2/66* (2006.01)
*C07K 14/415* (2006.01)

(52) U.S. Cl.
CPC .............. *A23L 2/66* (2013.01); *C07K 14/415* (2013.01)

(58) Field of Classification Search
CPC ... A23V 2002/00; A23V 2300/14; A23J 1/00; A23J 3/14
USPC ................................. 424/725, 400
See application file for complete search history.

(56) References Cited

U.S. PATENT DOCUMENTS

| | | | |
|---|---|---|---|
| 4,131,607 A | 12/1978 | Petit et al. | |
| 4,208,323 A | 6/1980 | Murray et al. | |
| 4,307,118 A | 12/1981 | Kajs | |
| 4,889,921 A | 12/1989 | Diosady et al. | |
| 5,086,166 A | 2/1992 | Lawhon et al. | |
| 5,844,086 A | 12/1998 | Murray et al. | |
| 6,005,076 A | 12/1999 | Murray et al. | |
| 6,630,195 B1 | 10/2003 | Muralidhara et al. | |
| 6,720,020 B2 | 4/2004 | Karleskind et al. | |
| 6,992,173 B2 | 1/2006 | Milanova et al. | |
| 7,001,990 B2 * | 2/2006 | Hiron et al. | 530/370 |
| 7,087,720 B2 | 8/2006 | Murray et al. | |
| 7,309,773 B2 | 12/2007 | Green et al. | |
| 2003/0125526 A1 | 7/2003 | Barker et al. | |
| 2004/0034200 A1 | 2/2004 | Logie et al. | |
| 2004/0039174 A1 | 2/2004 | Barker et al. | |
| 2004/0077838 A1 | 4/2004 | Green et al. | |
| 2004/0254353 A1 | 12/2004 | Barker et al. | |
| 2005/0107593 A1 | 5/2005 | Green et al. | |
| 2005/0165220 A1 | 7/2005 | Barker et al. | |
| 2005/0181112 A1 | 8/2005 | Schweizer et al. | |
| 2005/0220972 A1 | 10/2005 | Hiron | |
| 2005/0249828 A1 | 11/2005 | Logie et al. | |
| 2005/0255226 A1 * | 11/2005 | Schweizer et al. | 426/656 |
| 2006/0121171 A1 | 6/2006 | Schweizer et al. | |
| 2006/0281904 A1 | 12/2006 | Green et al. | |
| 2007/0004908 A1 | 1/2007 | Gosnell et al. | |
| 2007/0015910 A1 | 1/2007 | Barker et al. | |
| 2007/0065567 A1 | 3/2007 | Segall et al. | |
| 2007/0191593 A1 | 8/2007 | Green et al. | |
| 2007/0244300 A1 | 10/2007 | Schweizer et al. | |
| 2008/0125577 A1 | 5/2008 | Gosnell et al. | |
| 2008/0299282 A1 | 12/2008 | Schweizer et al. | |

FOREIGN PATENT DOCUMENTS

| | | |
|---|---|---|
| EP | 0289183 | 11/1988 |
| WO | WO 02/089597 | 11/2002 |
| WO | WO 03/043439 | 5/2003 |
| WO | WO 03/053157 | 7/2003 |
| WO | WO 03/088760 | 10/2003 |
| WO | WO 04/000031 | 12/2003 |
| WO | WO 2005/067729 | 7/2005 |
| WO | WO 2005/107492 | 11/2005 |
| WO | WO 2009/152620 | 12/2009 |

OTHER PUBLICATIONS

Tzeng Y.M. et al, "Production of Canola Protein Materials by Alkaline Extraction, Precipitation, and Membrane Procesisng", Jour. of Food Sci, vol. 55, No. 4, 1990, pp. 1147-1156.

Xu, L. et al, "The Production of Chinese Rapeseed Protein Isolates by Membrane Processing", Journal of American Oil Chemists Society, vol. 71, No. 9, 1994, pp. 935-939.

Murray D., "Rapeseed: A Potential Global Soruce of High Quality Plant Protein", Asia Pacific Food Industry, Apr. 2001, pp. 30-34.

Gillbert L., et al, "Preparation of Rapeseed Protein Isolate. Dissolution and Precipitation Behavior of Rapeseed Proteins", Jour. of Food Sci. 1976 vol. 41, pp. 1063-1069.

* cited by examiner

*Primary Examiner* — Chris R Tate
*Assistant Examiner* — Randall Winston
(74) *Attorney, Agent, or Firm* — William Kitt Sindey; Sim & McBurney

(57) ABSTRACT

Canola protein isolates are provided which contain both albumin and globulin protein fractions that are soluble, transparent and heat stable in an acidic aqueous environment. The canola protein isolates are completely soluble in water at low pH, low in phytic acid and useful in products for human consumption, pet foods and aquaculture.

4 Claims, No Drawings

SOLUBLE CANOLA PROTEIN ISOLATE PRODUCTION ("NUTRATEIN")

REFERENCE TO RELATED APPLICATION

"This application is a division of U.S. patent application Ser. No. 12/588,318 filed Oct. 13, 2009 which itself is a continuation-in-part of U.S. patent application Ser. No. 12/500,713 filed Jul. 10, 2009, which, in turn, claims priority under 35 USC 119 (e) from U.S. Provisional Patent Application No. 61/129,673 filed Jul. 11, 2008."

FIELD OF INVENTION

This invention relates to the production of canola protein isolate.

BACKGROUND TO THE INVENTION

Canola oil seed protein isolates having protein contents of at least 100 wt % (N×6.25) can be formed from oil seed meal by a process as described in copending U.S. patent application Ser. No. 10/137,391 filed May 3, 2002 (U.S. Patent Application Publication No. 2003-0125526A1 and WO 02/089597), and U.S. patent application Ser. No. 10/476,230 filed Jun. 9, 2004 (U.S. Patent Application Publication No. 2004-0254353A1), both assigned to the assignee hereof and the disclosures of which are incorporated herein by reference. The procedure involves a multiple step process comprising extracting canola oil seed meal using an aqueous salt solution, separating the resulting aqueous protein solution from residual oil seed meal, increasing the protein concentration of the aqueous solution to at least about 200 g/L while maintaining the ionic strength substantially constant by using a selective membrane technique, diluting the resulting concentrated protein solution into chilled water to cause the formation of protein micelles, settling the protein micelles to form an amorphous, sticky, gelatinous, gluten-like protein micellar mass (PMM), and recovering the protein micellar mass from supernatant having a protein content of at least about 100 wt % (N×6.25). As used herein, protein content is determined on a dry weight basis. The recovered PMM may be dried.

In one embodiment of the process, the supernatant from the PMM settling step is processed to recover canola protein isolate from the supernatant. This procedure may be effected by initially concentrating the supernatant using an ultrafiltration membrane and drying the concentrate. The resulting canola protein isolate has a protein content of at least about 90 wt %, preferably at least about 100 wt % (N×6.25).

The procedures described in U.S. patent application Ser. No. 10/137,391 are essentially batch procedures. In copending U.S. patent application Ser. No. 10/298,678 filed Nov. 19, 2002 (U.S. Patent Application Publication No. 2004-0039174A1 and WO 03/043439) and U.S. patent application Ser. No. 10/496,071 filed Mar. 15, 2005 (U.S. Patent Application Publication No. 2007-0015910), both assigned to the assignee hereof and the disclosures of which are incorporated herein by reference, there is described a continuous process for making canola protein isolates. In accordance therewith, canola oil seed meal is continuously mixed with an aqueous salt solution, the mixture is conveyed through a pipe while extracting protein from the canola oil seed meal to form an aqueous protein solution, the aqueous protein solution is continuously conveyed through a selective membrane operation to increase the protein content of the aqueous protein solution to at least about 50 g/L, while maintaining the ionic strength substantially constant, the resulting concentrated protein solution is continuously mixed with chilled water to cause the formation of protein micelles, and the protein micelles are continuously permitted to settle while the supernatant is continuously overflowed until the desired amount of PMM has accumulated in the settling vessel. The PMM is recovered from the settling vessel and may be dried. The PMM has a protein content of at least about 90 wt % (N×6.25), preferably at least about 100 wt %. The overflowed supernatant may be processed to recover canola protein isolate therefrom, as described above.

Canola seed is known to contain about 10 to about 30 wt % proteins and several different protein components have been identified. These proteins include a 12S globulin, known as cruciferin, a 7S protein and a 2S storage protein, known as napin. As described in copending U.S. patent application Ser. No. 10/413,371 filed Apr. 15, 2003 (U.S. Patent Application Publication No. 2004-0034200 and WO 03/088760) and U.S. patent application Ser. No. 10/510,766 filed Apr. 29, 2005 (U.S. Patent Application Publication No. 2005-0249828), assigned to the assignee hereof and the disclosures of which are incorporated herein by reference, the procedures described above, involving dilution of concentrated aqueous protein solution to form PMM and processing of supernatant to recover additional protein, lead to the recovery of isolates of different protein profiles.

In this regard, the PMM-derived canola protein isolate has a protein component composition of about 60 to about 98 wt % of 7S protein, about 1 to about 15 wt % of 12S protein and 0 to about 25 wt % of 2S protein. The supernatant-derived canola protein isolate has a protein component composition of about 60 to about 95 wt % of 2S protein, about 5 to about 40 wt % of 7S protein and 0 to about 5 wt % of 12S protein. Thus, the PMM-derived canola protein isolate is predominantly 7S protein and the supernatant-derived canola protein isolate is predominantly 2S protein. As described in the aforementioned U.S. patent application Ser. Nos. 10/413,371 and 10/510,766, the 2S protein has a molecular mass of about 14,000 daltons, the 7S protein has a molecular mass of about 145,000 daltons and the 12S protein has a molecular mass of about 290,000 daltons.

As described in copending U.S. patent application Ser. No. 11/038,086 filed Jan. 21, 2005 (WO 2005/067729) and Ser. No. 12/213,500 filed Jun. 20, 2008 (U.S. Patent Application Publication No. 2008/0299282), assigned to the assignee hereof and the disclosures of which are incorporated herein by reference, the supernatant-derived canola protein isolate can be treated to provide a form which has properties which are not shared by the supernatant-derived canola protein isolate, such properties including solubility at wide pH values and clarity in aqueous media. These properties enable the treated supernatant-derived canola protein isolate to be utilized to provide canola protein-fortified beverages, particularly at acid pH values.

Canola is also known as rapeseed or oil seed rape.

SUMMARY OF INVENTION

We have now found methods of producing a canola protein isolate containing both albumin and globulin protein fractions that is soluble and transparent and heat stable in an acidic aqueous environment while retaining the mild processing conditions of the above-described procedures but without precipitation of a protein micellular mass. The resulting canola protein isolate is not only completely soluble in water at low pH but also low in phytic acid. Heat stability in solution at low pH, permits thermal processing, such as hot fill applications. The canola protein isolate is useful in products for human consumption, such as for the protein fortification of, in particular, soft drinks and sports drinks, as well as other aqueous system, without precipitation of protein. The canola protein isolate is also useful for non-human food applications, such as pet foods and aquaculture.

In accordance with one aspect of the present invention, there is provided a method of producing a canola protein isolate having a canola protein content of at least about 90 wt % (N×6.25) d.b., preferably at least about 100 wt %, which comprises:

(a) extracting canola seed meal at a temperature of at least about 5° C. to cause solubilization of canola protein from the meal and to form an aqueous protein solution having a protein content of about 5 to about 40 g/L and a pH of about 5 to about 6.8, (b) separating the aqueous protein solution from the spent oil seed meal, (c) increasing the protein concentration of the aqueous protein solution to about 50 to about 250 g/L while maintaining the ionic strength substantially constant by using a selective membrane technique to provide a first concentrated protein solution, (d) optionally diafiltering the first concentrated protein solution, (e) adding calcium salt solution to the first concentrated protein solution to a conductivity of about 15 to about 25 mS to cause a precipitate to form in the first concentrated protein solution, (f) removing the precipitate from the first concentrated protein solution, (g) diluting the clarified first concentrated protein solution with about 2 to about 20, preferably about 10 to about 15, more preferably about 10, volumes of water having a temperature of about 2° to about 90° C., preferably about 10° to about 50° C., more preferably about 20° to about 30° C., (h) acidifying the resulting solution to a pH of about 2.5 to about 4.0 to produce an acidified clear protein solution, (i) increasing the concentration of the acidified clear protein solution to about 50 to about 250 g/L while maintaining the ionic strength substantially constant by using a selective membrane technique to provide a second concentrated protein solution, (j) optionally diafiltering the second concentrated protein solution, and (k) optionally drying the second concentrated protein solution to provide a canola protein isolate having a protein content of at least about 90 wt % (N×6.25) d.b., preferably at least about 100 wt % d.b.

A number of variations of this procedure may be adopted in accordance with the invention to result in the canola protein isolate composed of both albumin and globulin fractions that is soluble and transparent in an acidic aqueous environment.

In one such variation, the calcium chloride may be added to the aqueous protein solution following separation from the oil seed meal and prior to concentrating the solution. Following addition of the calcium chloride, the precipitate formed in the step is removed.

The resulting aqueous canola protein solution may be further processed by the steps of concentration, dilution, pH adjustment, further concentration and drying, as described above.

Accordingly, in another aspect of the present invention, there is provided a method of producing a canola protein isolate having a canola protein content of at least about 90 wt % (N×6.25) d.b., which comprises:

(a) extracting canola oil seed meal at a temperature of at least about 5° C. to cause solubilization of canola protein from the meal and to form an aqueous canola protein solution having a protein content of about 5 to about 40 g/L and a pH of about 5 to about 6.8, (b) separating the aqueous canola protein solution from the oil seed meal, (c) adding calcium salt solution to the aqueous protein solution to a conductivity of about 15 to about 25 mS, preferably about 17 to about 20 mS, to cause a precipitate to form in the canola protein solution, (d) removing the precipitate from the aqueous canola protein solution, (e) increasing the protein concentration of the aqueous protein solution to about 50 to about 250 g/L while retaining the ionic strength substantially constant by using a selective membrane technique to provide a concentrated protein solution, (f) optionally diafiltering the concentrated protein solution, (g) diluting the concentrated protein solution with about 2 to about 20, preferably about 10 to about 15, volumes of water having a temperature of about 2° to about 90° C., (h) acidifying the resulting solution to a pH of about 2.5 to about 4.0, preferably about 3 to about 3.5, to produce an acidified clear protein solution, (i) increasing the concentration of the acidified clear protein solution to about 50 to about 250 g/L while maintaining the ionic strength substantially constant by using a selective membrane technique to provide a second concentrated protein solution, (j) optionally diafiltering the second concentration protein solution, and (k) optionally drying the second concentrated protein solution to form a canola protein isolate having a protein content of at least about 90 wt % (N×6.25) d.b.

Alternatively, the resulting aqueous canola protein solution may be diluted to decrease the conductivity, such as by two volumes of water, and then adjusted in pH with HCl. The resulting solution may then be concentrated and diafiltered to further decrease the conductivity, resulting in a clear, low pH solution ready for drying.

In accordance with an additional aspect of the present invention, there is provided a method of producing a canola protein isolate having a canola protein content of at least about 90 wt % (N×6.25) d.b., which comprises:

(a) extracting canola oil seed meal at a temperature of at least about 5° C. to cause solubilization of canola protein from the meal and to form an aqueous canola protein solution having a protein content of about 5 to about 40 g/L and a pH of about 5 to about 6.8, (b) separating the aqueous canola protein solution from the oil seed meal, (c) adding calcium salt solution to the aqueous protein solution to a conductivity of about 15 to about 25 mS, preferably about 17 to about 20 mS, to cause a precipitate to form in the aqueous canola protein solution, (d) removing the precipitate from the aqueous canola protein solution, (e) diluting the aqueous canola protein solution with about 0.5 to about 10 volumes of water having a temperature of about 2° to about 90° C., (f) acidifying the resulting aqueous solution to a pH of about 2.5 to about 4.0 preferably to about 3 to about .3.5, to produce an acidified clear protein solution, (g) increasing the concentration of the acidified clear protein solution to about 50 to about 250 g/L while maintaining the ionic strength substantially constant by using a selective membrane technique to provide a concentrated protein solution, (h) optionally diafiltering the concentrated protein solution, and (i) optionally drying the concentrated protein solution to provide a canola protein isolate having a protein content of at least about 90 wt % (N×6.25) d.b.

In another such variation, the calcium chloride may be added to partially concentrated canola protein solution and the resulting precipitate removed from the partially concentrated canola protein solution. The clarified solution may then be put back on the membrane system for final concentration prior to the dilution, pH adjustment, further concentrating and drying steps described above.

In accordance with a further aspect of the present invention, there is provided a method of producing a canola protein isolate having a canola protein content of at least about 90 wt % (N×6.25) d.b., which comprises:

(a) extracting canola oil seed meal at a temperature of at least about 5° C. to cause solubilization of canola protein in the meal and to form an aqueous protein solution having a protein content of about 5 to about 40 g/L and a pH of about 5 to about 6.8, (b) separating the aqueous protein solution from the spent oil seed meal, (c) increasing the protein concentration of the aqueous protein solution to about 50 g/L or less while maintaining the ionic strength substantially constant by using a selective membrane technique to provide a partially concentrated protein solution, (d) adding calcium salt solution to the partially concentrated protein solution to a conductivity of about 15 to about 25 mS, preferably about 17 to about 20 mS, to cause a precipitate to form in the partially concentrated protein solution, (e) removing the precipitate from the partially concentrated protein solution, (f) further increasing the protein concentration of the partially concentrated protein solution to about 50 to about 250 g/L while maintaining the ionic strength substantially constant by using a selective membrane technique to provide a concentrated protein solution, (g) optionally diafiltering the concentrated protein solution, (h) diluting the concentrated protein solution with about 2 to about 20 volumes of water having a temperature of about 2° to about 90° C., (i) acidifying the resulting solution to a pH of about 2.5 to about 4.0, preferably about 3 to about 3.5, to produce an acidified clear protein solution, (j) increasing the concentration of the acidified clear protein solution to about 50 to about 250 g/L while maintaining the ionic strength substantially constant by using a selective membrane technique to provide a second concentrated protein solution, (k) optionally diafiltering the second concentrated protein solution, and (l) optionally drying the second concentrated protein solution to provide a canola protein isolate having a protein content of at least about 90 wt % (N×6.25) d.b.

Alternatively, the clarified partially concentrated canola protein solution may be diluted sufficiently to decrease the conductivity, pH adjusted and then concentrated and diafiltered prior to drying.

Accordingly, in a further aspect of the present invention, there is provided a method of producing a canola protein isolate having a protein content of at least about 90 wt % (N×6.25) d.b., which comprises:

(a) extracting canola oil seed meal at a temperature of at least about 5° C. to cause solubilization of canola protein from the meal and to form an aqueous protein solution having a protein content of about 5 to about 40 g/L and a pH of about 5 to about 6.8, (b) separating the aqueous protein solution from the spent oil seed meal, (c) increasing the protein concentration of the aqueous protein solution to about 50 g/L or less while maintaining the ionic strength substantially constant by using a selective membrane technique to provide a partially concentrated protein solution, (d) adding calcium salt solution to the concentrated protein solution to a conductivity of about 15 to about 25 mS, preferably about 17 to about 20 mS, to cause a precipitate to form in the partially concentrated protein solution, (e) removing the precipitate from the partially concentrated protein solution, (f) diluting the concentrated protein solution with about 0.5 to about 20 volumes of water having a temperature of about 2° to about 90° C., (g) acidifying the resulting solution to a pH of about 2.5 to about 4.0 preferably about 3 to about 3.5, to produce an acidified clear protein solution, (h) increasing the protein concentration of the acidified canola protein solution to about 50 to about 250 g/L while maintaining the ionic strength substantially constant by using a selective membrane technique to provide a concentrated protein solution, (i) optionally diafiltering the concentrated protein solution, and (j) optionally drying the concentrated protein solution to provide a canola protein isolate having a protein content of at least about 90 wt % (N×6.25) d.b.

In an additional such variant, aqueous calcium chloride solution can be used as the canola protein extraction salt to extract canola protein from the oil seed meal, which results in phytate being removed with the spent meal. The canola protein solution so produced may be diluted sufficiently with enough volumes of water to decrease the conductivity, then pH adjusted prior to concentrating and drying.

In accordance with another aspect of the present invention, there is provided a method of producing a canola protein isolate having a canola protein content of at least about 90 wt % (N×6.25) d.b., which comprises:

(a) extracting canola seed meal with an aqueous solution of a calcium salt, preferably having a concentration of less than about 1.0 M, more preferably about 0.1 to about 0.15 M, at a temperature of at least about 5° C. to cause solubilization of canola protein from the meal and to form an aqueous canola protein solution having a protein content of about 5 to about 40 g/L and a pH of about 5 to about 6.8, (b) separating the aqueous protein solution from the oil seed meal, (c) diluting the aqueous protein solution with about 0.5 to about 10 volumes of water having a temperature of about 2° to about 90° C., (d) acidifying the resulting diluted canola protein solution to a pH of about 2.5 to about 4, preferably about 3 to about 3.5, to produce an acidified clear protein solution, (e) increasing the concentration of the acidified clear protein solution to about 50 to about 250 g/L while maintaining the ionic strength substantially constant by using a selective membrane technique to provide a concentrated protein solution, (f) optionally diafiltering the concentrated protein solution, (g) optionally drying the concentrated solution to provide a canola protein isolate having a protein content of at least about 90 wt % (N×6.25) d.b.

The canola protein isolate produced according to the process herein may be used in conventional applications of protein isolates, such as, protein fortification of processed foods and beverages, emulsification of oils, body formers in baked goods and foaming agents in products which entrap gases. In addition, the canola protein isolate may be formed into protein fibers, useful in meat analogs, may be used as an egg white substitute or extender in food products where egg white is used as a binder. The canola protein isolate may be used as nutritional supplements. Other uses of the canola protein isolate are in pets foods, animal feed and in industrial and cosmetic applications and in personal care products.

GENERAL DESCRIPTION OF THE INVENTION

The initial step of the process of providing the canola protein isolate involves solubilizing proteinaceous material from canola oil seed meal. The proteinaceous material recovered from canola seed meal may be the protein naturally occurring in canola seed or the proteinaceous material may be a protein modified by genetic manipulation but possessing characteristic hydrophobic and polar properties of the natural protein. The canola meal may be any canola meal resulting from the removal of canola oil from canola oil seed with varying levels of non-denatured protein, resulting, for example, from hot hexane extraction or cold oil extrusion methods. The removal of canola oil from canola oil seed usually is effected as a separate operation from the protein isolate recovery procedure described herein.

Protein solubilization is effected most efficiently by using a food grade salt solution since the presence of the salt enhances the removal of soluble protein from the oil seed meal. Where the canola protein isolate is intended for non-food uses, non-food-grade chemicals may be used. The salt usually is sodium chloride, although other salts, such as, potassium chloride, may be used. The salt solution has a concentration of at least about 0.05 M, preferably at least about 0.10 M, to enable solubilization of significant quantities of protein to be effected. As the concentration of the salt solution increases, the degree of solubilization of protein in the oil seed meal initially increases until a maximum value is achieved. Any subsequent increase in concentration does not increase the total protein solubilized. The concentration of the food grade salt solution which causes maximum protein solubilization varies depending on the salt concerned. It is usually preferred to utilize a concentration value less than about 0.8 M, and more preferably a value of about 0.1 M to about 0.15 M.

In a batch process, the salt solubilization of the protein is effected at a temperature of from about 5° C. to about 75° C., preferably accompanied by agitation to decrease the solubilization time, which is usually about 10 to about 60 minutes. It is preferred to effect the solubilization to extract substantially as much protein from the oil seed meal as is practicable, so as to provide an overall high product yield.

The lower temperature limit of about 5° C. is chosen since solubilization is impractically slow below this temperature while the upper preferred temperature limit of about 75° C. is chosen due to the denaturation temperature of the protein.

In a continuous process, the extraction of the protein from the canola oil seed meal is carried out in any manner consistent with effecting a continuous extraction of protein from the canola oil seed meal. In one embodiment, the canola oil seed meal is continuously mixed with a food grade salt solution and the mixture is conveyed through a pipe or conduit having a length and at a flow rate for a residence time sufficient to effect the desired extraction in accordance with the parameters described herein. In such continuous procedure, the salt solubilization step is effected rapidly, in a time of up to about 10 minutes, preferably to effect solubilization to extract substantially as much protein from the canola oil seed meal as is practicable. The solubilization in the continuous procedure is effected at temperatures between about 10° C. and about 75° C., preferably between about 15° C. and about 35° C.

The aqueous food grade salt solution generally has a pH of about 5 to about 6.8, preferably about 5.3 to about 6.2, the pH of the salt solution may be adjusted to any desired value within the range of about 5 to about 6.8 for use in the extraction step by the use of any convenient acid, usually hydrochloric acid, or alkali, usually sodium hydroxide, as required.

The concentration of oil seed meal in the food grade salt solution during the solubilization step may vary widely. Typical concentration values are about 5 to about 15% w/v.

The protein extraction step with the aqueous salt solution has the additional effect of solubilizing fats which may be present in the canola meal, which then results in the fats being present in the aqueous phase.

The protein solution resulting from the extraction step generally has a protein concentration of about 5 to about 40 g/L, preferably about 10 to about 30 g/L.

The aqueous salt solution may contain an antioxidant. The antioxidant may be any convenient antioxidant, such as sodium sulfite or ascorbic acid. The quantity of antioxidant employed may vary from about 0.01 to about 1 wt % of the solution, preferably about 0.05 wt %. The antioxidant serves to inhibit oxidation of phenolics in the protein solution.

The aqueous phase resulting from the extraction step then may be separated from the residual canola meal, in any convenient manner, such as by employing a decanter centrifuge, followed by disc centrifugation and/or filtration to remove residual meal. The separated residual meal may be dried for disposal.

The colour of the final canola protein isolate can be improved in terms of light colour and less intense yellow by the mixing of powdered activated carbon or other pigment adsorbing agent with the separated aqueous protein solution and subsequently removing the adsorbent, conveniently by filtration, to provide a protein solution. Diafiltration also may be used for pigment removal.

Such pigment removal step may be carried out under any convenient conditions, generally at the ambient temperature of the separated aqueous protein solution, employing any suitable pigment adsorbing agent. For powdered activated carbon, an amount of about 0.025% to about 5% w/v, preferably about 0.05% to about 2% w/v, is employed.

Where the canola seed meal contains significant quantities of fat, as described in U.S. Pat. Nos. 5,844,086 and 6,005,076, assigned to the assignee hereof and the disclosures of which are incorporated herein by reference, then the defatting steps described therein may be effected on the separated aqueous protein solution and on the concentrated aqueous protein solution discussed below. When the colour improvement step is carried out, such step may be effected after the first defatting step.

As an alternative to extracting the canola oil seed meal with an aqueous salt solution, such extraction may be made using water alone, although the utilization of water alone tends to extract less protein from the canola oil seed meal than the aqueous salt solution. Where such alternative is employed, then the salt, in the concentrations discussed above, may be added to the protein solution after separation from the residual oil seed meal in order to maintain the protein in solution during the concentration step described below. When a first fat removal step is carried out, the salt generally is added after completion of such operations.

Another alternative procedure is to extract the canola oil seed meal with the food grade salt solution at a relatively high pH value above about 6.8, generally up to about 9.9. The pH of the food grade salt solution may be adjusted in pH to the desired alkaline value by the use of any convenient food-grade alkali, such as aqueous sodium hydroxide solution. Alternatively, the oil seed meal may be extracted with the salt solution at a relatively low pH below about pH 5, generally down to about pH 3. Where such alternative is employed, the aqueous phase resulting from the oil seed meal extraction step then is separated from the residual canola meal, in any convenient manner, such as by employing decanter centrifugation, followed by disc centrifugation and/or filtration to remove residual meal. The separated residual meal may be dried for disposal.

The aqueous protein solution resulting from the high or low pH extraction step then is pH adjusted to the range. of about 5 to about 6.8, preferably about 5.3 to about 6.2, as discussed above, prior to further processing as discussed below. Such pH adjustment may be effected using any convenient acid, such as hydrochloric acid, or alkali, such as sodium hydroxide, as appropriate.

The aqueous canola protein solution is concentrated to increase the protein concentration thereof while maintaining the ionic strength thereof substantially constant. Such concentration generally is effected to provide a concentrated protein solution having a protein concentration of about 50 to about 250 g/L, preferably about 200 g/L.

The concentration step may be effected in any convenient manner consistent with batch or continuous operation, such as by employing any convenient selective membrane technique, such as ultrafiltration or diafiltration, using membranes, such as hollow-fibre membranes or spiral-wound membranes, with a suitable molecular weight cut-off, such as about 3,000 to about 100,000 daltons, preferably about 5,000 to about 10,000 daltons, having regard to differing membrane materials and configurations, and, for continuous operation, dimensioned to permit the desired degree of concentration as the aqueous protein solution passes through the membranes.

As is well known, ultrafiltration and similar selective membrane techniques permit low molecular weight species to pass therethrough while preventing higher molecular weight species from so doing. The low molecular weight species include not only the ionic species of the food grade salt but also low molecular weight materials extracted from the source material, such as, carbohydrates, pigments and anti-nutritional factors, as well as any low molecular weight forms of the protein. The molecular weight cut-off of the membrane is usually chosen to ensure retention of a significant proportion of the protein in the solution, while permitting contaminants to pass through having regard to the different membrane materials and configurations.

The concentrated protein solution then may be subjected to a diafiltration step using an aqueous salt solution of the same molarity and pH as the extraction solution. Such diafiltration may be effected using from about 2 to about 20 volumes of diafiltration solution, preferably about 5 to about 10 volumes of diafiltration solution. In the diafiltration operation, further quantities of contaminants are removed from the aqueous canola protein solution by passage through the membrane with the permeate. The diafiltration operation may be effected until no significant further quantities of contaminants and visible colour are present in the permeate. Such diafiltration may be effected using the same membrane as for the concentration step. However, if desired, the diafiltration step may be effected using a separate membrane with a different molecular weight cut-off, such as a membrane having a molecular weight cut-off in the range of about 3,000 to about 100,000 daltons, preferably about 5,000 to about 10,000 daltons, having regard to different membrane materials and configuration.

An antioxidant may be present in the diafiltration medium during at least part of the diafiltration step. The antioxidant may be any convenient antioxidant, such as sodium sulfite or ascorbic acid. The quantity of antioxidant employed in the diafiltration medium depends on the materials employed and may vary from about 0.01 to about 1 wt %, preferably about 0.05 wt %. The antioxidant serves to inhibit oxidation of phenolics present in the concentrated canola protein isolate solution.

The concentration step and the diafiltration step may be effected at any convenient temperature, generally about 20° to about 60° C., preferably about 20 to about 30° C., and for the period of time to effect the desired degree of concentration. The temperature and other conditions used to some degree depend upon the membrane equipment used to effect the concentration and the desired protein concentration of the solution.

The concentrated and optionally diafiltered protein solution may be subject to a further defatting operation, if required, as described in U.S. Pat. Nos. 5,844,086 and 6,005,076.

The concentrated and optionally diafiltered protein solution may be subject to a colour removal operation as an alternative to the colour removal operation described above. Powdered activated carbon may be used herein as well as granulated activated carbon (GAC). Another material which may be used as a colour absorbing agent is polyvinyl pyrrolidone.

The colour absorbing agent treatment step may be carried out under any convenient conditions, generally at the ambient temperature of the canola protein solution. For powdered activated carbon, an amount of about 0.025% to about 5% w/v, preferably about 0.05% to about 2% w/v, may be used. Where polyvinylpyrrolidone is used as the colour absorbing agent, an amount of about 0.5% to about 5% w/v, preferably about 2% to about 3% w/v, may be used. The colour absorbing agent may be removed from the canola protein solution by any convenient means, such as by filtration.

The concentrated and optionally diafiltered canola protein solution resulting from the optional colour removal step may be subjected to pasteurization to reduce the microbial load. Such pasteurization may be effected under any desired pasteurization conditions. Generally, the concentrated and optionally diafiltered canola protein solution is heated to a temperature of about 55° to about 70° C., preferably about 60° to about 65° C., for about 10 to about 15 minutes, preferably about 10 minutes. The pasteurized concentrated canola protein solution then may be cooled for further processing as described below, preferably to a temperature of about 20° to about 35° C.

Following the concentration step and optional diafiltration, pigment removal and pasteurization steps, a food grade calcium salt, usually calcium chloride, is added to the resulting solution in order to prevent precipitation of micelles during the following dilution step. This addition causes the formation of a precipitate containing primarily calcium phytate. Sufficient calcium chloride is added to provide a solution having a conductivity generally of about 15 to about 25 mS, preferably of about 17 to about 20 mS. The calcium chloride may be added as a concentrated aqueous solution or in the dry form.

The addition of the calcium chloride may be effected at ambient temperature of about 20° to about 35° C., but a temperature in the range of about 5° to about 70° C. may be used. Following addition of the calcium chloride, the precipitated phytate is removed from the protein solution, such as by centrifugation.

The concentrated protein solution from the phytate precipitation is then diluted by mixing the retentate with water having a volume required to achieve the degree of dilution desired. As a result of the addition of calcium chloride, this dilution does not result in the precipitation of protein micelles. The concentrated protein solution generally is diluted about 2 to about 20 fold, preferably about 10 to about 15 fold.

The water with which the concentrated protein solution is mixed has a temperature of about 2° to about 90° C., preferably about 10° to about 50° C., more preferably about 20° to about 30° C.

The diluted retentate then is adjusted in pH to about 2.5 to about 4.0, preferably about 3 to about 3.5, by the addition of any suitable acid, such as hydrochloric acid, to result in a clear aqueous canola protein solution.

The clear aqueous canola protein solution is concentrated to increase the protein concentration thereof while maintaining the ionic strength thereof substantially constant. Such concentration generally is effected to provide a concentrated protein solution having a protein concentration of about 50 to about 250 g/L, preferably about 100 to about 150 g/L.

The concentration step may be effected in any convenient manner consistent with batch or continuous operation, such as by employing any convenient selective membrane technique, such as ultrafiltration or diafiltration, using membranes, such as hollow-fibre membranes or spiral-wound membranes, with a suitable molecular weight cut-off, such as about 3,000 to about 100,000 daltons, preferably about 5,000 to about 10,000 daltons, having regard to differing membrane materials and configurations, and, for continuous operation, dimensioned to permit the desired degree of concentration as the aqueous protein solution passes through the membranes.

The concentrated protein solution then may be subjected to a diafiltration step using water. The water may be at its natural pH, of a pH equal to the protein solution being diafiltered or any pH in between. Such diafiltration may be effected using from about 2 to about 20 volumes of diafiltration solution, preferably about 5 to about 10 volumes of diafiltration solution. In the diafiltration operation, further quantities of contaminants are removed from the clear aqueous canola protein solution by passage through the membrane with the permeate. The diafiltration operation may be effected until no significant further quantities of contaminants and visible colour are present in the permeate. Such diafiltration may be effected using the same membrane as for the concentration step. However, if desired, the diafiltration step may be effected using a separate membrane with a different molecular weight cut-off, such as a membrane having a molecular weight cut-off in the range of about 3,000 to about 100,000 daltons, preferably about 5,000 to about 10,000 daltons, having regard to different membrane materials and configuration.

An antioxidant may be present in the diafiltration medium during at least part of the diafiltration step. The antioxidant may be any convenient antioxidant, such as sodium sulfite or ascorbic acid. The quantity of antioxidant employed in the diafiltration medium depends on the materials employed and may vary from about 0.01 to about 1 wt %, preferably about 0.05 wt %. The antioxidant serves to inhibit oxidation of phenolics present in the concentrated canola protein isolate solution.

The concentration step and the diafiltration step may be effected at any convenient temperature, generally about 20° to about 60° C., preferably about 20° to about 30° C., and for the period of time to effect the desired degree of concentration. The temperature and other conditions used to some degree depend upon the membrane equipment used to effect the concentration and the desired protein concentration of the solution.

The concentrated and optionally diafiltered clear aqueous canola protein solution may be dried by any convenient technique, such as spray drying or freeze drying.

The pasteurization step described above may be effected on the canola protein solution prior to drying. The dry canola protein isolate has a high protein content, in excess of about 90 wt % protein, preferably at least about 100 wt % protein (calculated as N×6.25) on a dry weight basis. The canola protein isolate is low in phytic acid content, generally less than about 1.5% by weight.

As noted above, there are several variations on the procedure described herein to produce the canola protein isolate and involve several modifications to the steps outlined herein.

The canola protein isolate produced herein contains both albumin and globulin fractions and is soluble in an acidic aqueous environment, making the isolate ideal for incorporation into beverages, both carbonated and uncarbonated, to provide protein fortification thereto. Such beverages have a wide range of acidic pH values, ranging from about 2.5 to about 5. The canola protein isolate provided herein may be added to such beverages in any convenient quantity to provide protein fortification to such beverages, for example, at least about 5 g of the canola protein isolate per 12 fluid ounce quantity. The added canola protein isolate dissolves in the beverage and does not impair the clarity of the beverage, even after thermal processing. The canola protein isolate may be blended with dried beverage prior to reconstitution of the beverage by dissolution in water, even after thermal processing. The canola protein isolate may be blended with dried beverage prior to reconstitution of the beverage by dissolution in water.

EXAMPLES

Example 1

This Example describes the production of a novel canola protein isolate in accordance with one embodiment of the invention.

'a' kg of canola meal was added to 'b' L of 'c' M NaCl solution at ambient temperature and agitated for 30 minutes to provide an aqueous protein solution. The residual canola meal was removed and the resulting protein solution was partially clarified by centrifugation to produce 'd' L of partially clarified protein solution having a protein content of 'e' % by weight. The partially clarified protein solution was then filtered to further clarify resulting in a solution of volume 'f' L having a protein content of 'g' % by weight.

A 'h' L aliquot of the protein extract solution was reduced in volume to L by concentration on a Polyethersulfone (PES) membrane having a molecular weight cutoff of 'j' daltons and then diafiltered with 'k' L of 'l' M NaCl solution on the same membrane. The diafiltered retentate was then pasteurized at 60° C. for 10 minutes. The resulting pasteurized concentrated protein solution had a protein content of 'm' % by weight.

The concentrated solution was then adjusted to a conductivity of 'n' MS by the addition of food grade calcium chloride from a concentrated solution. The retentate was then centrifuged to remove precipitate formed upon calcium chloride addition. 'o' kg of precipitate was then re-suspended in 'p' L of 19 MS calcium chloride solution and centrifuged to recover as much solution protein as possible. The supernatant from the wash step was then combined with the treated retentate. In one of the examples, this wash procedure was repeated a second time. 'q' L of clarified retentate was then diluted into 'r' volumes of RO water. (Note: No micelles were formed when this dilution was carried out). This solution was then adjusted to a pH of 's' with HCL. The parameters 'a' to 't' for two runs are set forth in the following Table I:

TABLE I

|   | BW-SA082-C31-08a | BW-SA082-D14-08A |
|---|---|---|
| a | 20 | 20 |
| b | 200 | 200 |
| c | 0.15 | 0.15 |
| d | NA | 168 |
| e | 1.36 | 1.18 |
| f | 160 | 171 |
| g | 1.09 | 0.89 |
| h | 160 | 171 |
| i | 6.25 | 5 |
| j | 100,000 | 100,000 |
| k | 18.75 | 25 |
| l | 0.15 | 0.15 |
| m | 23.95 | 25.93 |
| n | 19.8 | 18.34 |
| o | 1.86 | 1.84 |
| p | 1.2 | 1.8 |
| q | 6.28 | 7.7 |
| r | 10 | 10 |
| s | 3 | 3 |

The pH adjusted clear solution was then reduced in volume to 't' L by ultrafiltration using a polyethersulfone (PES) membrane having a molecular weight cutoff of 'u' Daltons and then the concentrate was diafiltered on the same membrane with 'v' L of water. The diafiltered concentrate contained 'w' % protein by weight.

The overall protein recovery of the filtered protein solution was 'x' wt %. The concentrate was spray dried to form a final product given designation 'y' C700 and has a protein content of 'z' % (N×6.25) d.b. The parameters 't' to 'z' for two runs are set forth in the following Table II:

TABLE II

| y | BW-SA082-C31-08a | BW-SA082-D14-08A |
|---|---|---|
| t | 13.46 | 17 |
| u | 10,000 | 10,000 |
| v | 174 | 95 |
| w | 7.72 | 5.25 |
| x | 62 | 67 |
| z | 101 | 101 |

Example 2

This Example describes the production of a novel canola protein isolate in accordance with another aspect of the invention.

20 kg of canola meal was added to 200 L of 0.15 M NaCl solution at ambient temperature and agitated for 30 minutes to provide an aqueous protein solution. The residual canola meal was removed and the resulting protein solution was partially clarified by centrifugation to produce 153 L of partially clarified protein solution having a protein content of 1.30% by weight. The partially clarified protein solution was then filtered to further clarify resulting in a solution of volume 172 L having a protein content of 1.29% by weight.

The filtrate was then adjusted to a conductivity of 18.57 mS by the addition of food grade calcium chloride from a concentrated solution. The filtrate was then centrifuged to remove precipitate formed upon calcium chloride addition, providing 160 L of treated filtrate.

160 L of treated filtrate was reduced in volume to 6.88 L by concentration on a polyethersulfone (PES) membrane having a molecular weight cutoff of 100,000 Daltons. This sample was not diafiltered. The retentate was then pasteurized at 60° C. for 1 minute. The resulting pasteurized concentrated protein solution had a protein content of 19.44% by weight. The pasteurization step surprisingly resulted in notable protein precipitation.

6.74 L of pasteurized retentate was then diluted into 10 volumes of cold (3° C.) reverse osmosis purified water and the pH adjusted to 3 with HCl. The solution was then clarified by centrifugation and filtration, to remove solids believed formed in the pasteurization step.

The pH adjusted clear solution was then concentrated from 76.5 L to 20.5 kg by ultrafiltration using a polyethersulfone (PES) membrane having a molecular weight cutoff of 10,000 Daltons. No diafiltration was performed. The concentrated protein solution contained 4.08% protein by weight.

The overall protein recovery of the filtered protein solution was 37.8 wt %. The concentrate was carbon treated and spray dried to form a final product given designation BW-SA082-D21-08A C700FC, which had a protein content of 98.63% (N×6.25) d.b.

Example 3

This Example describes the production of a sample that, upon drying, would provide a novel canola protein isolate in accordance with another aspect of the invention.

60 kg of canola meal was added to 600 L of 0.15 M NaCl solution at ambient temperature and agitated for 30 minutes to provide an aqueous protein solution. The residual canola meal was removed and the resulting protein solution was partially clarified by centrifugation to produce 511 L of partially clarified protein solution having a protein content of 1.78% by weight. The partially clarified protein solution was then filtered to further clarify resulting in a solution of volume 534 L having a protein content of 1.51% by weight.

Sufficient calcium chloride was added to an aliquot of 500 ml of filtered protein solution to raise the conductivity to 20.6 mS. The $CaCl_2$ addition resulted in the formation of a white precipitate that was removed by centrifugation to provide a clear solution.

The treated and clarified protein solution was then diluted with 3 volumes of reverse osmosis purified water and the solution pH adjusted to 3.05 with HCl. No haze formed and the solution clarity remained high. The protein content of the diluted and acidified solution was 0.53% by weight.

1450 ml of the diluted and acidified solution was then reduced in volume to 200 ml on a Vivaflow 200 ultrafiltration unit equipped with a Hydrosart membrane having a molecular weight cut off of 10,000 daltons. The partially concentrated protein solution was then diafiltered on the same membrane with 200 ml of pH 3 reverse osmosis purified water to reduce the conductivity.

The diafiltered solution was then further concentrated to provide approximately 30 ml of clear retentate with a protein content of 12.39% by weight.

Example 4

This Example describes the production of a novel canola protein isolate in accordance with another aspect of the invention.

60 g of canola meal was added to 600 ml of 0.10 M $CaCl_2$ solution at ambient temperature and agitated for 30 minutes to provide an aqueous protein solution. The residual canola meal was removed and the resulting protein solution was clarified by centrifugation and filtration to produce 330 ml of clarified protein solution having a protein content of 1.17% by weight. The clarified protein solution was diluted with two volumes of reverse osmosis purified water to provide 990 ml of diluted solution having a protein content of 0.41% by weight. The pH of this solution was lowered to 3.03 by the addition of diluted hydrochloric acid. The protein solution was transparent after both the dilution and pH adjustment steps.

An aliquot of 920 ml of diluted and acidified protein solution was reduced in volume to 35 ml by concentration on a Vivaflow 200 ultrafiltration unit equipped with a Hydrosart membrane having a molecular weight cutoff of 10,000 daltons. The concentrated protein solution had a protein content of 6.84% by weight.

An aliquot of 32 ml of concentrated protein solution was diafiltered with 5 volumes of reverse osmosis purified water (160 ml) on the same membrane as used for the initial concentration step. The diafiltered and concentrated protein solution had a protein content of 7.06% by weight.

The overall protein recovery of the initial filtered protein solution was 60.4%. The diafiltered, concentrated protein solution was freeze dried to form a final product given the designation C701, which had a protein content of 93.42% (N×6.25) w.b.

SUMMARY OF THE DISCLOSURE

In summary of this disclosure, the present invention provides a novel procedure for forming a canola protein isolate composed of both albumin and globulin fractions that is soluble, heat stable and transparent in an acidic aqueous environment. Modifications are possible within the scope of this invention.

What we claim is:

1. A canola protein isolate having a protein content of at least about 90 wt % (N ×6.25) d.b. containing both albumin and globulin fractions of the canola protein and which is soluble in an acidic aqueous environment, prepared by a method which is selected from the group consisting of:

(A) (a) extracting canola oil seed meal at a temperature of at least about 5° C. to cause solubilization of canola protein from the meal and to form an aqueous protein solution having a protein content of about 5 to about 40 g/L and a pH of about 5 to about 6.8,
(b) separating the aqueous protein solution from the spent oil seed meal,
(c) increasing the protein concentration of the aqueous protein solution to about 50 to about 250 g/L while maintaining the ionic strength substantially constant by using a selective membrane technique to provide a first concentrated protein solution,
(d) optionally diafiltering the first concentrated protein solution,
(e) adding calcium salt solution to the first concentrated and optionally diafiltered protein solution to a conductivity of about 15 to about 25 mS to cause a precipitate to form in the first concentrated protein solution,
(f) removing the precipitate from the first concentrated protein solution,
(g) diluting the clarified first concentrated protein solution with about 2 to about 20 volumes of water having a temperature of about 2° to about 90° C.,
(h) acidifying the resulting solution to a pH of about 2.5 to about 4.0 to produce an acidified clear protein solution,
(i) increasing the concentration of the acidified clear protein solution to about 50 to about 200 g/L while maintaining the ionic strength substantially constant by using a selective membrane technique to provide a second concentrated protein solution,
(j) optionally diafiltering the second concentrated protein solution, and
(k) optionally drying the second concentrated protein solution to provide a canola protein isolate having a protein content of at least about 90 wt % (N ×6.25) d.b.;

(B) (a) extracting canola oil seed meal at a temperature of at least about 5° C. to cause solubilization of canola protein from the meal and to form an aqueous canola protein solution having a protein content of about 5 to about 40 g/L and a pH of about 5 to about 6.8,
(b) separating the aqueous canola protein solution from the oil seed meal,
(c) adding calcium salt solution to the aqueous protein solution to a conductivity of about 15 to about 25 mS to cause a precipitate to form in the concentrated protein solution,
(d) removing the precipitate from the aqueous canola protein solution,
(e) increasing the protein concentration of the aqueous protein solution to about 50 to about 250 g/L while retaining the ionic strength substantially constant by using a selective membrane technique to provide a first concentrated protein solution,
(f) optionally diafiltering the first concentrated protein solution,
(g) diluting the first concentrated protein solution with about 2 to about 20 volumes of water having a temperature of about 2° to about 90° C.,
(h) acidifying the resulting solution to a pH of about 2.5 to about 4.0 to produce an acidified clear protein solution,
(i) increasing the concentration of the acidified clear protein solution to about 50 to about 250 g/L while maintaining the ionic strength substantially constant by using a selective membrane technique to provide a second concentrated protein solution,
(j) optionally diafiltering the second concentration protein solution, and
(k) optionally drying the second concentrated protein solution to provide a canola protein isolate having a protein content of at least about 90 wt % (N ×6.25) d.b.;

(C) (a) extracting canola oil seed meal at a temperature of at least about 5° C. to cause solubilization of canola protein from the meal and to form an aqueous protein solution having a protein content of about 5 to about 40 g/L and a pH of about 5 to about 6.8, (b) separating the aqueous protein solution from the spent oil seed meal, (c) increasing the protein concentration of the aqueous protein solution to about 50 g/L or less while maintaining the ionic strength substantially constant by using a selective membrane technique to provide a partially concentrated protein solution, (d) adding calcium salt solution to the partially concentrated protein solution to a conductivity of about 15 to about 25 mS to cause a precipitate to form in the partially concentrated protein solution, (e) removing the precipitate from the partially concentrated protein solution, (f) further increasing the protein concentration of the partially concentrated protein solution to about 50 to about 250 g/L while maintaining the ionic strength substantially constant by using a selective membrane technique to provide a first concentrated protein solution, (g) optionally diafiltering the first concentrated protein solution, (h) diluting the first concentrated protein solution with about 2 to about 20 volumes of water having a temperature of about 2° to about 90° C., (i) acidifying the resulting solution to a pH of about 2.5 to about 4.0 to produce an acidified clear protein solution, (j) increasing the concentration of the acidified clear protein solution to about 50 to about 250 g/L while maintaining the ionic strength substantially constant by using a selective membrane technique to provide a second concentrated protein solution, (k) optionally diafiltering the second concentrated protein solution, and (l) optionally drying the second concentrated protein solution to provide a canola protein isolate having a protein content of at least about 90 wt % (N ×6.25) d.b.;

(D) (a) extracting canola seed meal with an aqueous solution of a calcium salt at a temperature of at least about 5° C. to cause solubilization of canola protein from the meal and to form an aqueous canola protein solution having a protein content of about 5 to about 40 g/L and a pH of about 5 to about 6.8, (b) separating the aqueous protein solution from the oil seed meal, (c) diluting the aqueous protein solution with about 0.5 to about 10 volume of water having a temperature of about 2° to about 90° C., (d) acidifying the resulting diluted canola protein solution to a pH of about 2.5 to about 4 to produce an acidified clear protein solution, (e) increasing the concentration of the acidified clear protein solution to about 50 to about 250 g/L while maintaining the ionic strength substantially constant by using a selective membrane technique to provide a concentrated protein solution, (f) optionally diafiltering the concentrated protein solution, (g) optionally drying the concentrated solution to provide a canola protein isolate having a protein content of at least about 90 wt % (N ×6.25) d.b.;

(E) (a) extracting canola oil seed meal at a temperature of at least about 5° C. to cause solubilization of canola protein from the meal and to form an aqueous protein solution having a protein content of about 5 to about 40 g/L and a pH of about 5 to about 6.8, (b) separating the aqueous protein solution from the spent oil seed meal, (c) increasing the protein concentration of the aqueous protein solution to about 50 g/L or less while maintaining the ionic strength substantially constant by using a selective membrane technique to provide a partially concentrated protein solution, (d) adding calcium salt solution to the partially concentrated protein solution to a conductivity of about 15 to about 25 mS to cause a precipitate to form in the partially concentrated protein solution, (e) removing the precipitate from the partially concentrated protein solution, (f) diluting the partially concentrated protein solution with about 0.5 to about 20 volumes of water having a temperature of about 2 to about 90° C., (g) acidifying the resulting solution to a pH of about 2.5 to about 4.0 to produce an acidified clear protein solution, (h) increasing the protein concentration of the acidified canola protein solution to about 50 to about 250 g/L while maintaining the ionic strength substantially constant by using a selective membrane technique to provide a concentrated protein solution, (i) optionally diafiltering the concentrated protein solution, and (j) optionally drying the concentrated protein solution to provide a canola protein isolate having a protein content of at least about 90 wt % (N ×6.25) d.b.; and (F) (a) extracting canola oil seed meal at a temperature of about 5° C. to cause solubilization of canola protein from the meal and to form an aqueous canola protein solution having a protein content of about 5 to about 40 g/L and a pH of about 5 to about 6.8, (b) separating the aqueous canola protein solution from the oil seed meal, (c) adding calcium salt solution to the aqueous protein solution to a conductivity of about 15 to about 25 mS to cause a precipitate to form in the concentrated protein solution, (d) removing the precipitate from the aqueous canola protein solution, (e) diluting the aqueous canola protein solution with about 0.5 to about 10 volumes of water having a temperature of about 2° to about 90° C., (f) acidifying the resulting aqueous solution to a pH of about 2.5 to 4.0 to produce an acidified clear protein solution, (g) increasing the concentration of the acidified clear protein solution to about 50 to about 250 g/L while maintaining the ionic strength substantially constant by using a selective membrane technique to provide a concentrated protein solution, (h) optionally diafiltering the concentrated protein solution, and (i) optionally drying the concentrated protein solution to provide a canola protein isolate having a protein content of at least about 90 wt % (N ×6.25) d.b.

2. The canola protein isolate of claim 1 wherein the acidic aqueous environment is a beverage having a pH ranging from about 2.5 to about 5.

3. The canola protein isolate of claim 1 having a phytic acid content of less than about 1.5% by weight.

4. The canola protein isolate of claim 1 having a protein content of at least about 100 wt % (N ×6.25) d.b.

* * * * *